US012672783B2

(12) United States Patent
Odame et al.

(10) Patent No.: US 12,672,783 B2
(45) Date of Patent: Jul. 7, 2026

(54) LUNG FUNCTION MONITORING FROM HEART SIGNALS

(71) Applicant: THE TRUSTEES OF DARTMOUTH COLLEGE, Hanover, NH (US)

(72) Inventors: Kofi M. Odame, Hanover, NH (US); Maria T. Nyamukuru, West Lebanon, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 549 days.

(21) Appl. No.: 17/538,347

(22) Filed: Nov. 30, 2021

(65) Prior Publication Data

US 2022/0167856 A1 Jun. 2, 2022

Related U.S. Application Data

(60) Provisional application No. 63/120,085, filed on Dec. 1, 2020.

(51) Int. Cl.
*A61B 5/0205* (2006.01)
*A61B 5/00* (2006.01)
(Continued)

(52) U.S. Cl.
CPC ........ *A61B 5/0205* (2013.01); *A61B 5/02416* (2013.01); *A61B 5/053* (2013.01);
(Continued)

(58) Field of Classification Search
CPC ... A61B 5/0205; A61B 5/318; A61B 5/02416; A61B 5/053; A61B 5/0816; A61B 5/091; G16H 40/67; G06N 3/04
(Continued)

(56) References Cited

U.S. PATENT DOCUMENTS 5,174,286 A * 12/1992 Chirife ............... A61N 1/36514
607/11
7,610,094 B2 * 10/2009 Stahmann .............. A61B 5/103
607/42
(Continued)

FOREIGN PATENT DOCUMENTS

WO WO-2017032873 A2 * 3/2017 ............. A61B 5/746

OTHER PUBLICATIONS

Odame et al., "Can a wearable device detect airway obstruction?", IEEE Open Journal of Engineering in Medicine and Biology, Nov. 2020, 5 pages.
(Continued)

*Primary Examiner* — Michael J Lau
(74) *Attorney, Agent, or Firm* — Quarles & Brady, LLP

(57) ABSTRACT

A breathing monitor has ECG, PPG, or bioimpedance sensors feeding a neural network to provide inspiratory and expiratory phases of breathing and tidal volume (TV), filters for the inspiratory and expiratory phases of breathing and TV; and apparatus configured to provide measurements of breathing rate (RR), and fractional inspiratory time (FIT). In embodiments, the device uses the RR, FIT, and TV to estimate spirometric parameters such as lung obstruction severity, forced expiratory volume in one second (FEV1), forced expiratory volume (FEV), forced vital capacity (FVC), FEV1/FEV ratio, and FEV1/FVC ratio. A method of determining a classification of lung obstruction from heart signals includes feeding heart signals into a neural network to determine TV and inspiratory and expiratory classes used to determine FIT and RR; and using FIT, RR, and TV to determine lung obstruction classification of mild, moderate, severe, or very severe obstructive symptoms.

7 Claims, 4 Drawing Sheets

ECG    preprocess

Multi-Task Learning – Gated Recurrent Neural Network

Inspiratory & Expiratory Class Labels duty cycle resp. signal freq. count respiratory features

F.I.T.

R.R.

52

(51) Int. Cl.

| | |
|---|---|
| *A61B 5/024* | (2006.01) |
| *A61B 5/053* | (2021.01) |
| *A61B 5/08* | (2006.01) |
| *A61B 5/091* | (2006.01) |
| *A61B 5/318* | (2021.01) |
| *G06N 3/04* | (2023.01) |
| *G16H 40/67* | (2018.01) |

(52) U.S. Cl.
CPC ............ *A61B 5/0816* (2013.01); *A61B 5/091* (2013.01); *A61B 5/318* (2021.01); *A61B 5/4842* (2013.01); *A61B 5/7267* (2013.01); *G06N 3/04* (2013.01); *G16H 40/67* (2018.01)

(58) Field of Classification Search
USPC ......................................................... 600/301
See application file for complete search history.

(56) References Cited

U.S. PATENT DOCUMENTS

| | | | | |
|---|---|---|---|---|
| 8,221,327 | B2 * | 7/2012 | Lee ...................... | A61B 5/4818 600/529 |
| 9,031,793 | B2 * | 5/2015 | Lynn ...................... | G16H 20/17 702/19 |
| 9,042,952 | B2 * | 5/2015 | Lynn ...................... | A61B 5/087 600/324 |
| 9,521,971 | B2 * | 12/2016 | Lynn ................... | A61B 5/0205 |
| 10,702,166 | B1 * | 7/2020 | Freeman ............. | A61B 5/0205 |
| 2005/0209521 | A1 * | 9/2005 | Kettunen ............ | A61B 5/0205 600/508 |
| 2012/0330177 | A1 * | 12/2012 | Al-Rawas ............. | A61B 5/091 600/533 |
| 2018/0271440 | A1 * | 9/2018 | Yun ...................... | A61B 5/4884 |
| 2018/0336970 | A1 * | 11/2018 | Sherwood .......... | G01N 33/4975 |
| 2019/0167176 | A1 * | 6/2019 | Annoni ............... | A61B 5/0823 |
| 2019/0167209 | A1 * | 6/2019 | Annoni ............... | A61B 5/0826 |
| 2020/0054520 | A1 * | 2/2020 | Johnson ............... | A61B 5/091 |
| 2020/0121252 | A1 * | 4/2020 | Weber ................. | A61B 5/6801 |
| 2020/0135334 | A1 * | 4/2020 | Rajasekhar ........... | G06N 3/084 |
| 2020/0138337 | A1 * | 5/2020 | Choi ...................... | A61B 5/082 |
| 2020/0253547 | A1 * | 8/2020 | Harris ................. | A61B 5/7203 |
| 2020/0329977 | A1 * | 10/2020 | Freeman ............. | A61B 5/0205 |

OTHER PUBLICATIONS

Milagro et al. "Electrocardiogram-Derived Tidal Volume During Treadmill Stress Test", IEEE Transactions of Biomedical Engineering, vol. 67, No. 1, Jan. 2020, 10 pages.

* cited by examiner

PRIOR ART

Normal respiratory profile $$FIT = \frac{t_i}{t_i + t_e} \approx 0.45$$

Inspiratory phase $t_i$

Expiratory phase $t_e$

Respiratory phase $t_r$

Time (s)

Obstructed respiratory profile $$FIT = \frac{t_i}{t_i + t_e} \approx\, < 0.3$$

Inspiratory phase $t_i$

Expiratory phase $t_e$

Time (s)

Respiratory phase $t_r$

LUNG FUNCTION MONITORING FROM HEART SIGNALS

PRIORITY CLAIM

The present document claims priority to U.S. Provisional Patent Application 63/120,085, filed Dec. 1, 2020. The entire contents of the aforenamed provisional patent application are incorporated herein by reference.

BACKGROUND

Airway obstruction in obstructive lung diseases, including chronic obstructive pulmonary disease (COPD) and asthma, is not constant. For example, in COPD, obstruction in chronic bronchitis and emphysema may vary with time, and asthma often involves "attacks" where obstruction may be far more severe than the patient's normal condition. Monitoring lung airway obstruction—a condition where inflammation and excess mucus production in the lungs' airways impedes airflow—is critical for early detection of symptom flare-ups and possible infections in obstructive lung disease, in COPD these flare-ups and infections are known as exacerbations. If we detect and treat these attacks or COPD exacerbations early, it will increase patients' quality of life, reduce mortality, and potentially eliminate billions of dollars in healthcare costs because exacerbations and asthma attacks can lead to hospitalizations that can sometimes be avoided with prompt outpatient treatment. It is also desirable to monitor patients to determine whether medication dosages and types are appropriate or need modification.

It is important to monitor asthma-related obstruction because patient reports and symptom logs are often inaccurate, and because symptoms often vary with activity, environmental conditions including inhaled allergens, food allergens, and viral infections. Asthma can not only lead to infections and result in expensive emergency room visits, but severe asthma attacks can themselves be fatal. Asthma is often controlled with a combination of short-acting medications such as beta agonists, and longer-acting "controller" medications such as inhaled or oral steroids that frequently have undesirable side effects. With good patient monitoring asthma medications can be adjusted to both minimize undesirable side effects of medications and keep attack frequency and pulmonary obstruction to tolerable levels.

Ideally, early detection of COPD exacerbation and treatment by monitoring, or monitoring of asthma, requires measurements be made outside medical facilities, such as at home.

The state-of-the-art for measuring lung function at home is hand-held spirometry, a technique hindered by low patient adherence and often by poor patient technique. In response, some authors propose to monitor lung health with mobile and wearable technology. Approaches taken include physical activity monitoring, and accelerometer-based assessment of cardiorespiratory function. These approaches can distinguish between healthy controls and patients with lung disease, but they provide no information on a patient's severity level of lung airway obstruction—a continually changing measure that is critical for assessing disease progression and exacerbations.

A few researchers have explored ways to infer severity of airway obstruction from non-spirometric data, such as CT scans, that cannot be measured with a wearable device. As they are not wearable, they are unsuitable for continuous patient monitoring.

There is a growing infrastructure of smartwatches, smartphones and wearable devices that can measure heart activity via electrocardiography (ECG) or photoplethysmography (PPG). It is also possible to measure heart activity with bioimpedance sensors. Some PPG devices can also measure breathing rate. While breathing rate can provide a coarse picture of lung health, it is inadequate for inferring more detailed information, like the extent and severity of lung airway obstruction. Respiration affects the rhythm and electrical activity of the heart; these changes can be sensed with ECG or PPG or a combination of ECG and PPG and used to extract breathing rate from the ECG and PPG signals.

For purposes of this document, "heart signals" include heart activity signals sensed with ECG, PPG, or bioimpedance sensors.

A person experiencing lung airway obstruction will take longer than usual to exhale, as illustrated in FIG. 1. This is reflected in an abnormally short fractional inspiratory time (FIT). FIT is defined as the duration of the inspiratory phase as a fraction of the total respiratory period. FIT drops from a normal range of 0:45-0:5 to as low as 0:2 in the presence of severe airway obstruction.

Traditionally, lung function is measured by spirometry in laboratories. Spirometry reports measures including Forced Vital Capacity (FVC), Forced Expiratory Volume (FEV), Forced Expiratory Volume in one second (FEV1), and ratios like FEV1/FEV that are of diagnostic significance to pulmonologists and other physicians.

SUMMARY

In an embodiment, a breathing monitor device has an ECG, PPG, or bioimpedance sensor feeding an electronic neural network that provides signals representing inspiratory and expiratory phases of breathing and tidal volume (TV), filters for the signals representing inspiratory and expiratory phases of breathing and TV; and apparatus configured to receive the filtered signals and to provide measurements of breathing rate (RR), and fractional inspiratory time (FIT). In embodiments, the device also has an apparatus configured to use the RR, FIT, and TV to estimate spirometric parameters selected from one of lung obstruction, a forced expiratory volume in one second (FEV1), a forced expiratory volume (FEV), a forced vital capacity (FVC), a FEV1/FEV ratio, and a FEV1/FVC ratio.

In another embodiment, a method of determining a classification of lung obstruction based upon heart signals includes feeding heart signals from a subject into a neural network to determine a TV and inspiratory and expiratory classes that are used to determine a FIT and an RR; and using the FIT, RR, and TV to determine a lung obstruction classification indicating the subject has mild, moderate, severe, or very severe obstructive symptoms.

3 polynomial regression classifier, or a neural network classifier, to determine a level of airway obstruction, according to embodiments.

Figure 3:
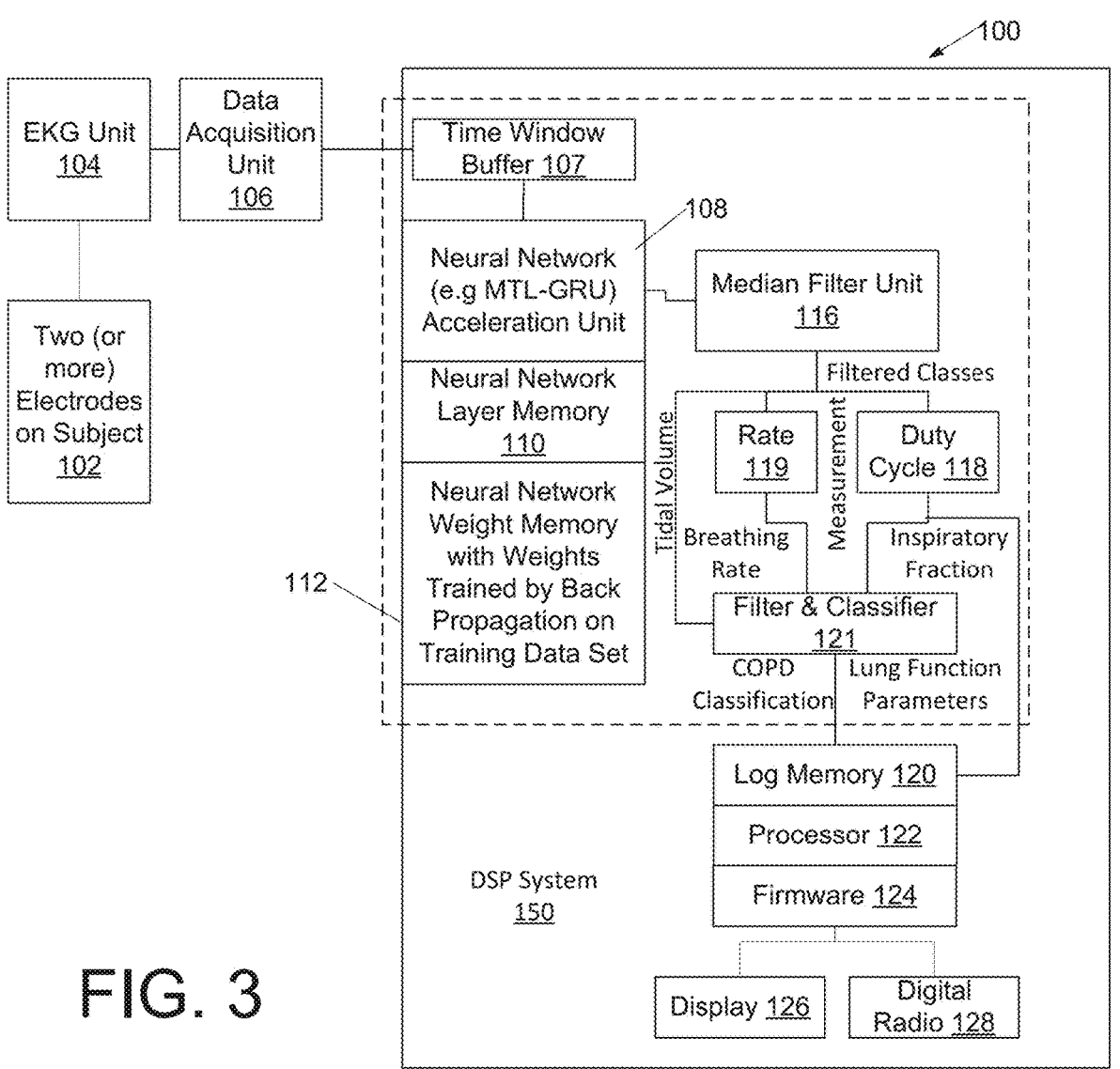
FIG. 3 is a detailed block diagram of an embodiment of a lung function monitor device using a neural network, such as a gated recurrent unit (GRU) neural network, to extract lung function parameters from electrocardiographic signals, and a classifier, such as a KNN classifier, SVM classifier.
Figure 4:
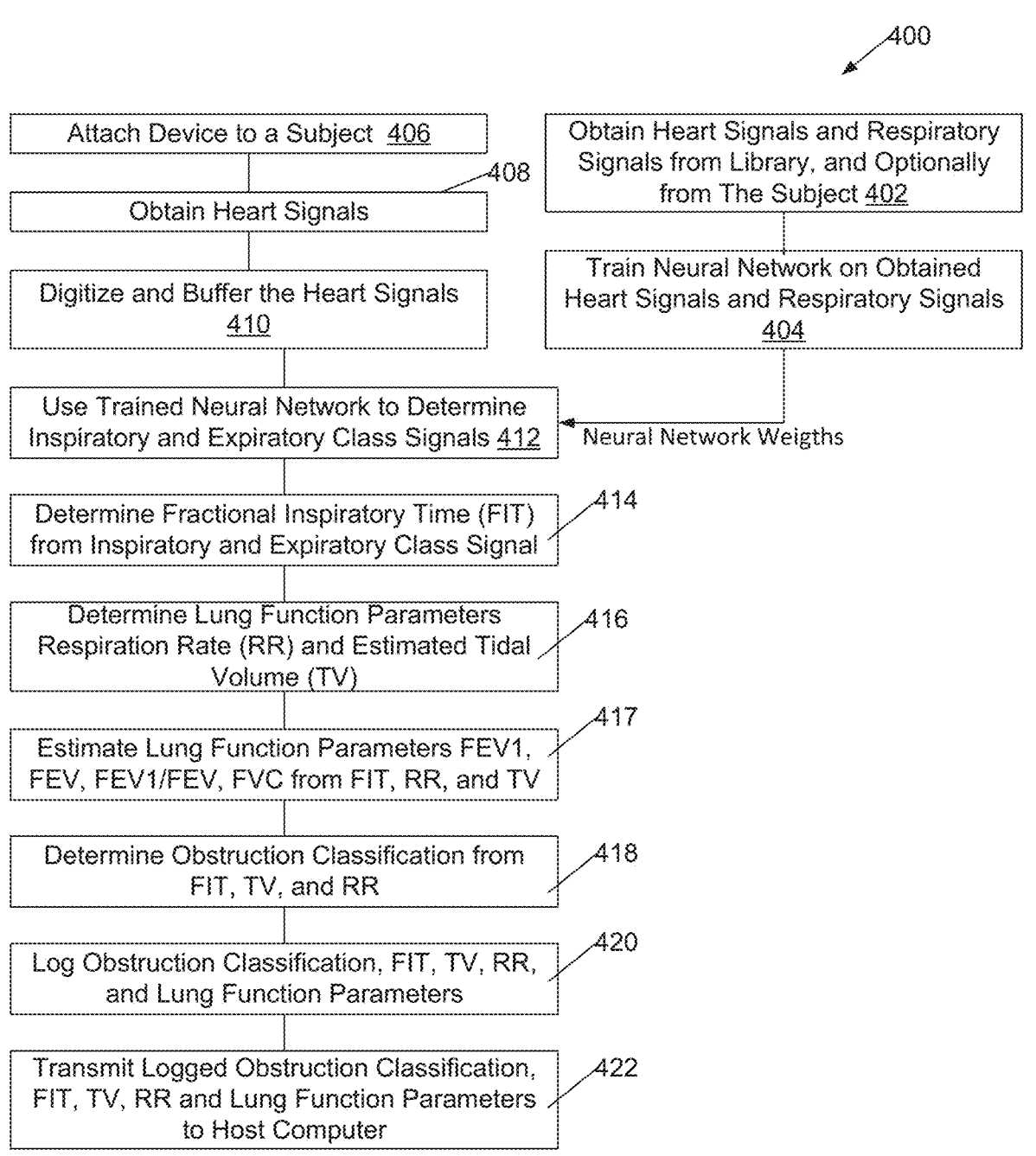

FIG. 4 is a flowchart of a method of classifying obstructive lung symptoms using the device of FIG. 3, according to embodiments.

DETAILED DESCRIPTION OF THE EMBODIMENTS

Remote and continuous monitoring of lung function is useful for the early detection of and monitoring of respiratory diseases. Lung function monitoring is mostly estimated from respiratory signals. Respiration affects heart signals, and as such, we derive measures of lung function from heart signals measurable in a wearable device. The heart signals are obtained from a subject or patient wearing the device. The device monitors lung function by estimating important pulmonary function parameters from the heart signals. The pulmonary factors assessed include some or all of fractional inspiratory time (FIT), inspiratory/expiratory ratio (I/E ratio or IER), forced vital capacity (FVC), forced expiratory volume (FEV), forced expiratory volume in one second (FEV1), and tidal volume (TV). These parameters are used to monitor lung function and infer a degree of airway obstruction. The heart signals used to estimate these parameters include Electrocardiogram (ECG) signals, may include photoplethysmogram (PPG) (sometimes known as pulse oximetry) signals, and, in some embodiments, may include bioimpedance images of heart-related movements. Specifically, we extract the duration of the inspiratory and expiratory phases of the respiratory cycle from these heart signals; in an embodiment the duration of inspiratory and expiratory phases of the respiratory cycle are determined by analyzing the temporal dependencies in ECG over multiple time scales with a gated recurrent neural network (GRU).

We have found alterations to the ECG between expiratory and inspiratory phases of the respiratory cycle in turn produce subtle changes to the ECG signal. For instance, the amplitude envelope of the ECG's "R peaks" is modulated during the breathing cycle due to changes in the heart's position as the diaphragm expands and contracts. When airway obstruction increases the exhalation time, this is reflected by a longer positive half cycle in the ECG's amplitude modulation envelope. Also, the heart rate increases during inhalation and decreases during exhalation due to pressure changes in the thoracic cavity. So, longer-than-usual exhalation times caused by airway obstruction produce corresponding longer periods of lowered heart rate that are observable in the ECG or PPG signal. Similarly, oxygen saturation levels observed by PPG may vary through the respiratory cycle.

As illustrated in FIG. 3, a particular embodiment of the device includes an ECG unit 104 that receives electrical signals through at least two skin electrodes 102 positioned on a subject, the electrical signals originating from the subject's heart. The ECG unit 104 provides preprocessed signals through a data acquisition unit 106 as digitized heart signals to a digital signal processing (DSP) system 150 that performs data logging, data processing, and data export.

Figure 1:
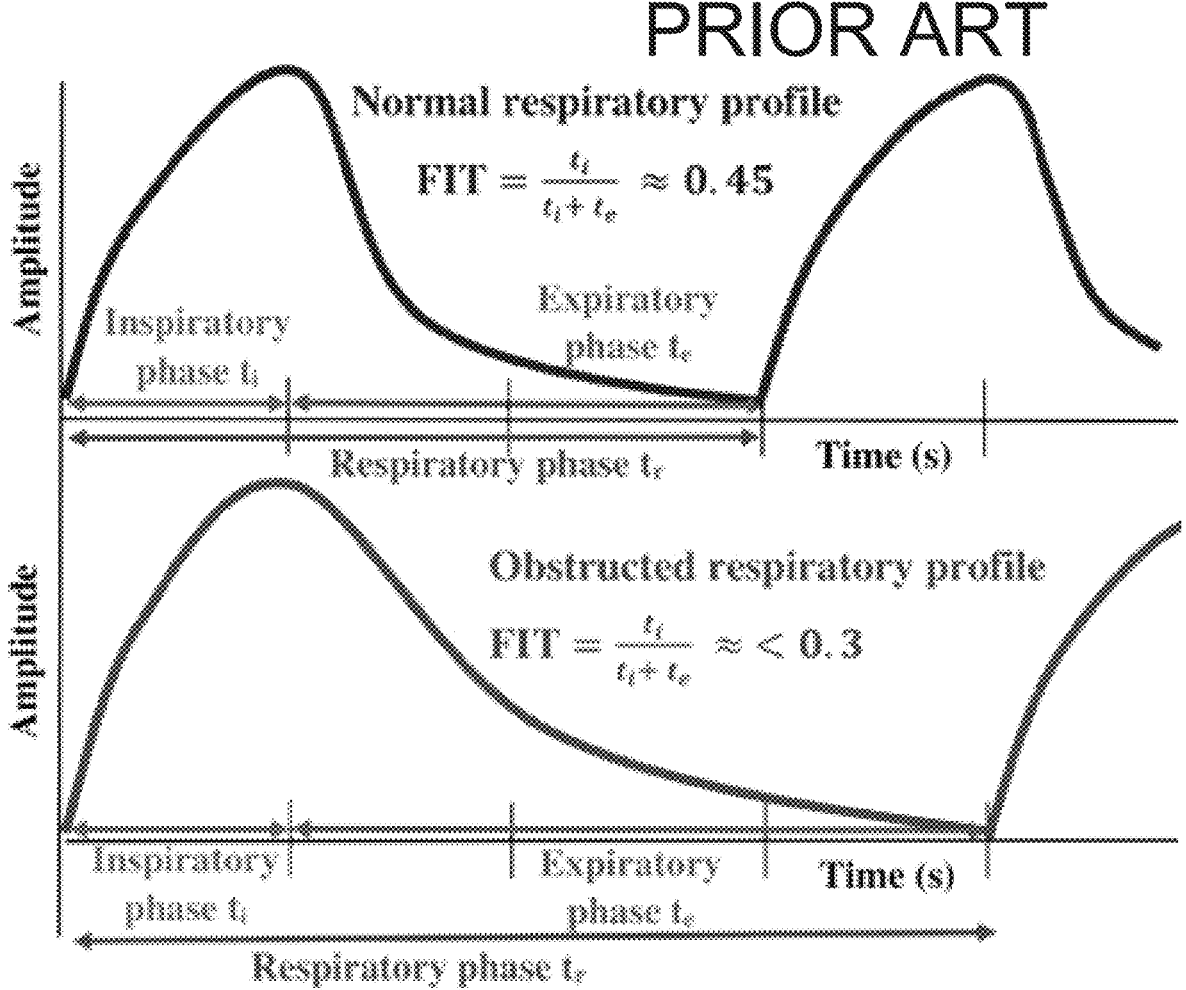
FIG. 1 is an illustration of inspiratory and expiratory phases in a typical breath cycle, as known in the art.
Figure 2:
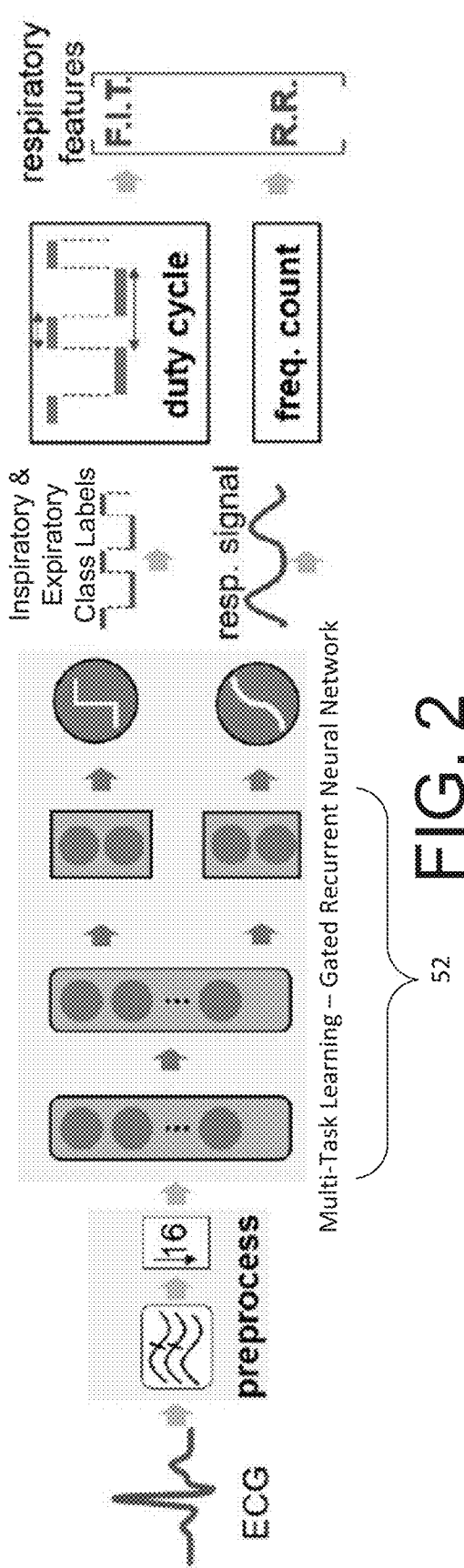
FIG. 2 is a high-level data flow diagram of an embodiment of a method for extracting a fractional inspiratory time (FIT) and respiration rate (RR) from electrocardiogram (ECG) data, according to embodiments.

The DSP system 150 takes the digitized heart signals as input and classifies the inspiration and expiration phases of the underlying respiratory signals from the heart signals. In embodiments, the classification of heart signals into inspiratory and expiratory phases is done by a neural network 52, 108, as illustrated in FIG. 2 and FIG. 3, that, in embodiments, is a Gated Recurrent Unit (GRU) neural network that has three hidden GRU layers followed by two fully connected (FC) layers; other embodiments may have four, five, or more GRU layers. In additional embodiments, neural network 52, 108 is a convolutional neural network or a long short-term memory (LSTM) neural network, used to extract inspiratory and expiratory phases from the heart signals. In yet other embodiments, other techniques such as heuristic algorithms may be used to extract inspiratory and expiratory phase information from the digitized heart signals.

The difference in amplitude of ECG R waves between inspiratory peaks and expiratory valleys is a function of respiratory tidal volume (TV); this and other effects permit training the neural network 52, 108 to extract an estimated TV from the heart signals.

In embodiments, the neural network 52, 108 is a GRU neural network trained on temporally aligned heart signals, TV, and a signal representing two phases of respiratory signals, where a first phase signal represents the inspiration phase, and a second phase signal represents the expiration phase of respiration during which the temporally aligned heart signals were recorded. In embodiments, the temporally aligned heart signals and respiratory signals for training the neural network are obtained from a library of heart signals and respiratory measurements and signals obtained from a variety of patients having a range of obstructive lung symptoms from normal to severe obstruction. In a particular embodiment, in addition to training the GRU neural network on a training set of temporally aligned heart signals and respiratory signals obtained from a library of heart signals with corresponding spirometric measurements of tidal volume, FEV1, and FVC, the GRU neural network is also trained on heart signals and respiratory signals obtained from a particular subject or patient for whom the device is being configured and for whom the device is prescribed and who will be the subject or patient wearing the device. Once the network is trained, typically on a workstation computer, the weights determined are saved in a neural network weight memory 110 of the device.

The neural network provides a phase class output indicating inspiratory phase versus expiratory phase that is used to calculate the fractional inspiratory time (FIT) and respiratory rate. The neural network also outputs an estimated tidal volume (TV). The FIT is calculated for every complete breathing cycle, as is a respiratory rate (RR). A complete breathing cycle includes an entire inspiration phase and expiration phase. The FIT provides a direct measurement of airway obstruction and is combined in a classifier with the respiratory rate and tidal volume to estimate the lung function parameters; forced expiratory volume (FEV), forced expiratory volume in one second (FEV1), forced vital capacity (FVC), and tidal volume (TV); and to estimate a severity of a subject's obstructive lung disease, including severity of COPD, asthmatic obstruction, or other lung disease. In alternative embodiments, the inspiratory phase and expiratory phase signal(s) are used to generate an inspiratory/expiratory ratio (I/E ratio or IER) that is used in place of FIT as a measurement of airway obstruction in estimating other measures of lung function and estimating a severity of a subject's COPD. In embodiments, the classifier is a K-Nearest-Neighbors (KNN) classifier. In alternative embodiments, the classifier is another trainable classifier such as a support vector machines (SVM) classifier, a second neural network, or a polynomial regression-based classifier.

What makes this device novel is the estimation of FIT, followed by determination of obstructive lung symptoms severity, from ECG or other heart signals.

The extraction of FIT from heart signals makes it such that we can use existing and prevalent technology and devices that are used to monitor heart signals to also monitor lung function.

Heart signal sensors are typically noisy, which jeopardizes the FIT estimation and therefore reduces the accuracy of the lung function monitoring. This challenge can be addressed by designing robust digital filters and increasing redundancy in the heart signal sensors. These improvements are projected to result in an estimation error that is comparable to spirometry, the current gold standard.

As a technology for analyzing pulmonary signs, the invention is useful in a broad range of respiratory disease applications, such as COVID-19 and other pneumonia monitoring and treatment, lung transplant post-operative care, and respiratory therapy research, that require continuous, objective, and unobtrusive monitoring of pulmonary function changes. Since the invention is compatible with low-cost microcontrollers, it has the potential to dominate the spirometry market and respiratory clinical trials space with high-volume production.

In an exemplary embodiment (FIG. 3) of a portable heart and breathing monitor device 100, at least two, and in some embodiments only two, electrodes 102 are positioned on a subject (not shown) in positions where they can acquire electrocardiographic (ECG) signals from the subject. The ECG signals are fed to ECG unit 104 where they are amplified and digitized in data acquisition unit 106; in a particular embodiment these signals are digitized into digital ECG signals at 30 analog-to-digital conversions per second. These signals are fed to a data DSP unit 150 where they are captured in a time window buffer 107. In a particular embodiment, the ECG signals are filtered by a bandpass filter having a low frequency cutoff of 0.05 hertz and a high frequency cutoff of 50 hertz before being captured in the time window buffer 107. The time window buffer 107 collects digitized ECG signals for a time window expected to be longer than most breathing cycles. In an embodiment, the time window buffer 107 may be 20 seconds to a minute long and, in a particular embodiment, 25 seconds long.

Digitized ECG signals for each time window are fed to a neural network that, in a particular embodiment, is a Multi-Task Learning-Gated Recurrent Unit (MTL-GRU) neural network 108 that is implemented in software in some embodiments and may, in some embodiments, be implemented in a hardware neural network acceleration unit. The neural network includes a layer memory 110 that holds current values for each simulated neuron of each layer of the neural network, and a weight memory 112 configured with the weights previously determined by backpropagation during training with the training set on a similar neural network running on a workstation, as previously described. The weights include weights for each synapse of the neural network. The neural network provides classified signals indicative of inspiration and expiration breathing phases to a median filtering unit 116 that provides filtered class labels to a duty cycle measurement unit 118, which provides a FIT. After the digitized heart signals of an entire time window are fed to the neural network, the neural network state memory is reset for the next time window. Median filtering unit 116 filters class labels, breathing rates, and tidal volume across multiple time windows.

In alternative embodiments, the GRU neural network is replaced with either a convolutional neural network or a long short-term memory (LSTM) neural network. In these alternative embodiments, as with the GRU neural network, each neural network has at least three layers, and in embodiments 3, 4, 5, or 6 layers, all configured with synapse weights in a weight memory; the synapse weights determined by back propagation in a similar neural network executing on a workstation while training on the training set previously described.

The sum of inspiratory time and expiratory time provides a measure of respiration period, which can be inverted in a rate measurement unit 119 to provide a respiration rate RR. Measured duty cycles provide breathing-related signals including an inspiratory fraction FIT and breathing rate, along with the tidal volume TV, to a data logging memory 120 where they are recorded with a current time tag. ECG signals from ECG unit 104 or PPG signals, may also have pulse rate and other characteristics such as arrhythmias measured and logged in data logging memory 120, however these data paths are not detailed in FIG. 3. In addition to logging TV, FIT and RR, FIT, TV, and RR or respiration period are input to a classifier 121 that filters measured TV, FIT and RR and compares measured TV, FIT and RR against TV, FIT and RR determined from other recent breathing cycles to drop TV, FIT and RR measurements that are anomalous, then classifies the filtered TV, FIT and RR or respiratory period as representative of mild, moderate, severe, or very severe lung obstruction, or of mild, moderate, severe, or very severe COPD. In embodiments, the classifier further derives other lung parameters, including one or more of FEV1/FEV or FEV1/FVC, FEV1, FEV, from the TV, FIT, and RR or respiration period. The lung obstruction and/or COPD classification is also logged in logging memory 120 with times of the measurements so a time progression of disease or exacerbations can be determined by a physician who downloads data from the log memory 120 through digital radio 128. As previously stated, the classifier is selected from a decision tree classifier, random forest classifiers, a KNN classifier, a SVM classifier, a neural network, a polynomial regression classifier, etc.

A processor 122 is provided with firmware 124 to control operation of the entire heart and breathing monitor device 100, including executing functions of the DSP or controlling operation of neural network acceleration hardware that performs the neural network functions, and to provide inspiratory fraction, breathing rate, tidal volume, pulse rate, and other arrhythmias, and the other lung function parameters selected from FEV1/FEV, FVC, and FEV1/FVC in human readable form on display 126 and in machine readable form via digital radio 128 to cell phones and computers where they may be further processed so a physician can monitor the subject's health, a server can update the subject's health records, and alert medical personnel when logged lung function parameters exceed safe limits for the subject.

In an embodiment, the GRU network has three 16-unit hidden GRU layers, one 16-unit fully connected layer, and a single unit output layer. The network processes 25-second long (7500 samples at a 300 sample-per-second sampling rate) sequences in a sampling window, the sequence sampled at 30, 300, or another rate between 30 and 300, samples per second, and returns output for each sample in the sequence. Before calculating the FIT, the duty cycle measurement unit 118 identifies the number of complete cycles (Nc) in the 25-second window. A complete cycle includes an inspiratory phase and an expiratory phase. The duty cycle measurement unit 118 computes the FIT for each complete respiration cycle $FIT=Ni/Ntot$ where Ni is the number of samples in the inspiratory phase and Ntot is the total number of samples in the complete respiration cycle, which is the sum of samples in the inspiratory and expiratory phases of breathing.

Respiratory rate is computed for each 25-second window as Fs=60×Nc/Stot, where Fs is the sampling frequency Nc is the total number of complete cycles in each window and Stot is the total number of samples in each complete 25-second window.

Tidal volume is estimated by the neural network from differences in peak R-wave amplitude, respiratory rate, pulse rate, and pulse rate variability of ECG. We note that pulse rate, pulse rate variability, and respiratory rate can also be derived from PPG signals or bioimpedance signals and used by a neural network to estimate tidal volume.

It is desirable that the window sampled and processed to determine respiratory rate and FIT be greater in length than most breaths. In alternative embodiments, longer windows than 25 seconds are used within the range 20 to 60 seconds in width.

The device of FIG. 3 is operated according to a method 400, with reference to FIG. 4. Heart signals, such as ECG or PPG signals, and respiration signals are obtained 402 from a library, which is a multi-patient database, and in a particular embodiment supplemented with additional heart signals and respiration signals from a particular subject to whom the device is being tailored. A neural network corresponding to the neural network embodied in the device 150 is trained 404 on the obtained signals to generate neural network weights. The neural network weights are programmed into the device weight memory to allow independent function and wearability of the device.

The device is then attached 406 to the subject and heart signals corresponding to those extracted from the database but obtained 408 directly from the subject wearing the device. These heart signals are digitized and buffered 410, then fed to the neural network to determine 412 inspiratory and expiratory class signals and tidal volume (TV) signals. These inspiratory and expiratory class signals are then used 414 to determine fractional inspiratory time (FIT) and to determine 416 respiration rate (RR). Lung function parameters are estimated 417. The TV, FIT and RR are used to determine 418 a COPD classification indicating the subject has mild, moderate, severe, or very severe lung obstruction symptoms and, in some embodiments, to estimate other lung function parameters such as FEV1/FEV, FEV1/FVC, FEV1, FEV, or FVC. The estimated lung function parameters, TV, FIT, RR, and obstruction classification are logged 420 in memory of the device and transmitted 422 to a host device such as a host computer or cell phone from which alerts may be sent to medical personnel.

In embodiments, a correlation matrix was generated for the relation between measured tidal breathing parameters (fractional inspiratory time, respiratory rate, and estimated tidal volume) and the spirometric parameters (FEV1/FVC or FEV1/FEV, FEV1, and FVC).

We used results of the correlation analysis to identify which of the tidal breathing measures would be useful as a predictor variable in estimating each spirometric parameter. The tidal breathing measures with the highest correlation coefficients were used to predict FEV1/FVC, FEV1 and FVC via multiple regression. In one particular embodiment, it was found:

$$FEV1/FVC=0.094+1.57 \cdot FIT-0.227 \cdot RR$$

$$FEV1=-1.16+5.35 \cdot FIT+0.005 \cdot TV$$

$$FVC=1.55+0.0096 \cdot TV$$

In alternative embodiments, a fitting operation is used to fit coefficients of a first, second, or third order equation, such as C1, C2, and C3 of an equation like FEV1/FVC=C1+C2*FIT+C3*RR to data from the training set. In other alternative embodiments, a neural network classifier is used to generate the spirometric parameters from the measured FIT, RR, and TV, the neural network classifier being trained on the training set described above.

In one embodiment, a k-nearest neighbor (KNN) classifier is used to detect the absence or presence of lung airway obstruction, using FIT, RR and TV as the predictor variables, and applying the GOLD criteria on FEV1/FVC to obtain the true class labels. The tidal breathing parameters were also used to classify the severity of airway obstruction. Since this is an ordinal classification problem, in one embodiment, we used a classifier that is based on a regression model (independent variables: FIT, RR, TV; dependent variable: percent-age predicted FEV1). The regression model's estimated FEV1 score was used to classify airway obstruction severity, according to the GOLD criteria to distinguish between all four severity levels of mild, moderate, severe, and very severe obstruction.

In alternative embodiments, other forms of classifier are used, including a neural network classifier trained on extracted FIT, TV, and RR with spirometric data from the training set.

Changes may be made in the above system, methods or device without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method of operating a breathing monitor to determine a classification of lung obstruction or inflammation based upon heart signals from a subject, comprising:

at a processor of the breathing monitor, receiving heart signals acquired from the subject using a heart sensor selected from the group consisting of an electrocardiographic (ECG) sensor, a photoplethysmographic (PPG) sensor, and a bioimpedance sensor;

processing the heart signals using a neural network to generate inspiratory and expiratory class signals based on the digital heart signals and to generate tidal volume signals as a function of peaks and valleys of waveforms corresponding to the inspiratory and expiratory class signals;

determining, via the processor of the breathing monitor, at least one of a force expiratory volume in one second (FEV1) or a forced vital capacity (FVC) using the inspiratory and expiratory class signals and tidal volume signals;

using the FEV1 or the FVC to determine, via the processor of the breathing monitor, a lung obstruction or inflammation classification indicating the subject has mild, moderate, severe, or very severe obstructive or inflammation symptoms;

logging, via the processor of the breathing monitor, the lung obstruction or inflammation classification to create a time progression of the disease; and outputting, from the breathing monitor, a medical alert based on the determined lung obstruction or inflammation classification.

2. The method of claim 1, wherein the weights in the weight memory are previously determined by training a corresponding neural network on a multi-patient database of heart signals and respiration signals.

3. The method of claim 2, wherein the multi-patient database further comprises electrocardiographic and respiration signals obtained from the subject.

4. The method of claim 2, wherein the heart signals comprise signals from a sensor selected from the group consisting of an electrocardiographic (ECG) sensor, a photoplethysmographic (PPG) sensor, and a bioimpedance sensor.

5. The method of claim 4, wherein determining the lung obstruction classification or inflammation is performed with a classifier selected from the group consisting of decision tree classifiers, random forest classifiers, K-nearest-neighbors (KNN) classifiers, neural network classifiers, and support vector machines classifiers.

6. The method of claim 1, wherein the neural network is selected from the group consisting of a gated recurrent unit (GRU) neural network, a convolutional neural network, and a long short-term memory (LSTM) neural network.

7. The method of claim 1, wherein neural network is further trained on obtained signals to modify the weights in the weight memory.

* * * * *